(12) United States Patent
Yang et al.

(10) Patent No.: US 11,395,605 B2
(45) Date of Patent: Jul. 26, 2022

(54) SUPPORTING STRUCTURE APPLYING GRAVITY COMPENSATION MECHANISM AND IMPACT CONTROL SYSTEM HAVING THE SUPPORTING STRUCTURE

(71) Applicant: KOREA INSTITUTE OF SCIENCE AND TECHNOLOGY, Seoul (KR)

(72) Inventors: Sungwook Yang, Seoul (KR); Eui Sung Yoon, Seoul (KR); Hoon Ryu, Seoul (KR); Hyeonjoo Im, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 703 days.

(21) Appl. No.: 16/385,244

(22) Filed: Apr. 16, 2019

(65) Prior Publication Data
US 2019/0320941 A1 Oct. 24, 2019

(30) Foreign Application Priority Data
Apr. 19, 2018 (KR) .......... 10-2018-0045492

(51) Int. Cl.
*G01L 5/00* (2006.01)
*A61B 5/103* (2006.01)
*A61B 5/00* (2006.01)

(52) U.S. Cl.
CPC .......... *A61B 5/1036* (2013.01); *A61B 5/4064* (2013.01); *G01L 5/0052* (2013.01); *A61B 2503/40* (2013.01); *A61B 2503/42* (2013.01)

(58) Field of Classification Search
CPC . A61B 5/1036; A61B 5/4064; A61B 2503/40; A61B 2503/42; G01L 5/0052
See application file for complete search history.

(56) References Cited

U.S. PATENT DOCUMENTS

| 4,605,379 | A | * | 8/1986 | Shahan | ...................... H01J 9/00 445/59 |
| 5,094,595 | A | * | 3/1992 | Labrador | .............. F03B 13/182 60/506 |
| 5,183,344 | A | * | 2/1993 | Pawlak | ...................... B41J 9/36 400/157.2 |
| 9,808,193 | B2 | | 11/2017 | Tortella et al. | |

(Continued)

FOREIGN PATENT DOCUMENTS

| CN | 2543060 Y | 4/2003 |
| KR | 10-0986289 B1 | 10/2010 |

(Continued)

OTHER PUBLICATIONS

Michael A Flierl et al., "Mouse closed head injury model induced by a weight-drop device", Nature Protocols, 2009, pp. 1328-1337, vol. 4, No. 9.

(Continued)

*Primary Examiner* — Max H Noori
(74) *Attorney, Agent, or Firm* — Rabin & Berdo, P.C.

(57) ABSTRACT

An impact control system includes a supporting structure with gravity compensation mechanism, and a supporting bed which is supported by the supporting structure and supports an impact target. Here, the supporting structure includes an elastic element, a vertical support to which one end of the elastic element is fixed, a horizontal support to which the other end of the elastic element is fixed, and which is rotatable around a rotation axis disposed at one end of the horizontal support meeting an end of the vertical support, and a weight support part which is connected to the other end of the horizontal support and supports the supporting bed while contacting a lower surface of the supporting bed.

7 Claims, 6 Drawing Sheets

(56) References Cited

U.S. PATENT DOCUMENTS

| | | | |
|---|---|---|---|
| 2002/0045518 A1* | 4/2002 | Dalebout | A63B 22/02 |
| | | | 482/51 |
| 2004/0195775 A1* | 10/2004 | Goldsmith, Jr. | F41J 7/04 |
| | | | 273/392 |
| 2005/0051179 A1 | 3/2005 | Foong et al. | |
| 2014/0107523 A1 | 4/2014 | Petraglia et al. | |
| 2017/0176308 A1 | 6/2017 | Koning | |
| 2021/0283476 A1* | 9/2021 | Carr | G01P 15/04 |
| 2022/0024523 A1* | 1/2022 | Schneider | B62D 25/20 |
| 2022/0029484 A1* | 1/2022 | Takahashi | H02K 15/06 |

FOREIGN PATENT DOCUMENTS

| | | |
|---|---|---|
| KR | 10-1292005 B1 | 8/2013 |
| KR | 2016-0138540 A | 12/2016 |
| WO | WO 2015/151035 A1 | 10/2015 |

OTHER PUBLICATIONS

Tsung-Hsun Hsieh et al., "Relationship of mechanical impact magnitude to neurologic dysfunction severity in a rat traumatic brain injury model", Plos One, May 26, 2017, pp. 1-18.

Dhananjay R. Namjoshi et al., "Merging pathology with biomechanics using CHIMERA (Closed-Head Impact Model of Engineered Rotational Acceleration): a novel, surgery-free model of traumatic brain injury", Molecular Neurodegeneration, 2014, pp. 1-18, vol. 9, No. 55.

Johan Davidsson et al., "A new model to produce sagittal plane rotational induced diffuse axonal injuries", Frontiers in Neurology, Jun. 2011, pp. 1-11, vol. 2, Article 41.

Michael J. Kane et al., "A mouse model of human repetitive mild traumatic brain injury", Journal of Neuroscience Methods, 2012, pp. 41-49, vol. 203.

* cited by examiner

SUPPORTING STRUCTURE APPLYING GRAVITY COMPENSATION MECHANISM AND IMPACT CONTROL SYSTEM HAVING THE SUPPORTING STRUCTURE

CROSS-REFERENCE TO RELATED APPLICATION

This application claims priority to Korean Patent Application No. 10-2018-0045492, filed on Apr. 19, 2018, and all the benefits accruing therefrom under 35 U.S.C. § 119, the contents of which in its entirety are herein incorporated by reference.

BACKGROUND

1. Field

The present disclosure relates to a supporting structure with gravity compensation mechanism and an impact control system having the same, and more particularly, to a supporting structure for applying a desired impact to an object without the rebound effect by the application of gravity compensation mechanism and an impact control system employing the structure.

2. Description of the Related Art

The need for systems for precisely applying impacts for the purpose of experiments and treatments has been raised. In particular, there is discussion about precise impact control systems for animal experiments to study changes in human body caused by external impacts such as traumatic brain injury (TBI).

The traumatic brain injury refers to a brain tissue injury caused by an external mechanical impact or acceleration/deceleration of the brain, and causes consciousness disorders or changes and consequential injuries of cognition function or physical function.

The traumatic brain injury affects about 1.7 million of related patients each year in the United States, and considerable direct/indirect costs related to the traumatic brain injury are incurred, so it is raised as a big medical/economical/social issue. No matter how mild it is, brain injury is likely to develop degenerative brain diseases such as Parkinson's disease and dementia later.

It is a weight-drop model that is widely used in animal experiments to study the traumatic brain injury. In the weight-drop model, an anesthetized animal is placed on a sponge bed and is impacted on the head by a free fall of a weight disposed on top along a guide tube. This process can be implemented in a simple manner, but its problem is the rebound effect that the weight strikes the head again by the elastic property of the wire on which the weight hangs after the impact, dissimilar to the real impact situation.

Accordingly, especially in the areas of traumatic brain injury research, there is a need for a precise impact control system free of the rebound effect for animal experiments to study the brain tissue injury mechanism.

RELATED LITERATURES

Patent Literatures (Patent Literature 1) U.S. Pat. No. 9,808,193

SUMMARY

The present disclosure is designed to solve the above-described problem, and therefore the present disclosure is directed to providing a supporting structure with gravity compensation mechanism for precisely applying a desired amount of impact without the rebound effect and an impact control system having the same.

To achieve the above-described object, according to an aspect of the present disclosure, an impact control system includes a supporting structure with gravity compensation mechanism, and a supporting bed which is supported by the supporting structure and supports an impact target. The supporting structure includes an elastic element, a vertical support to which one end of the elastic element is fixed, a horizontal support to which the other end of the elastic element is fixed, and which is rotatable around a rotation axis disposed at one end of the horizontal support meeting an end of the vertical support, and a weight support part which is connected to the other end of the horizontal support and supports the supporting bed while contacting a lower surface of the supporting bed.

According to an embodiment of the present disclosure, each of the vertical support and the horizontal support may include a sliding hole.

According to an embodiment of the present disclosure, a guide to which one end of the elastic element is fixed may be configured to be moveable along the sliding hole of the vertical support, a guide to which the other end of the elastic element is fixed may be configured to be moveable along the sliding hole of the horizontal support, and a supportable mass of the target may be changed by moving the guides of the elastic element.

According to an embodiment of the present disclosure, the elastic element may be a spring.

According to an embodiment of the present disclosure, the supporting bed may include two support plates, and each of the support plates may have one end of a hinge structure.

According to an embodiment of the present disclosure, when an impact is applied to the target, the weight support part of the supporting structure may move down to allow the two support plates of the supporting bed to split down and the target to fall down.

According to an embodiment of the present disclosure, each of the support plates may include a hole formed by removing a central area of the plate.

The supporting structure according to various embodiments of the present disclosure can stably support a target having a predetermined range of masses. Additionally, the proposed impact control system can apply an impact without the rebound effect. Through this, it is possible to precisely apply a desired impact similarly to the real environment and observe changes on cell and tissue levels occurring differently depending on an amount of impact, and it can be used to study the relationship with related diseases and treat the diseases.

The effects obtainable from the present disclosure are not limited to the above-mentioned effects, and other effects not mentioned herein will be clearly understood by those skilled in the art from the following description.

DETAILED DESCRIPTION

The advantages and features of the present disclosure and the methods for achieving the same will be apparent from the embodiments described below in detail with reference to the accompanying drawings. However, the present disclosure is not limited to the embodiments disclosed below and will be embodied in a variety of different forms, these embodiments are provided so that the present disclosure will be thorough and complete and will fully convey the scope of the present disclosure to those skilled in the art, and the present disclosure is defined by the scope of the appended claims.

The shape, size, proportion, angle and number shown in the accompanying drawings to describe the embodiments of the present disclosure are for illustration purposes only, and the present disclosure is not limited to the illustrations. Additionally, in describing the present disclosure, a certain detailed description of relevant known technology is determined to render the key subject matter of the present disclosure unnecessarily ambiguous, the detailed description is omitted herein. The terms "comprising", "including" and "having" when used in this specification do not preclude the presence or addition of other elements unless the term 'only' is used herein. As used herein, the singular forms are intended to include the plural forms as well, unless the context clearly indicates otherwise.

In the interpretation of the elements, it is interpreted as including an error range unless the context clearly indicates otherwise.

In the description of the positional relationship, for example, the positional relationship between two elements using 'on', 'above', 'below', 'next to', etc., one or more other elements may be interposed between the two elements unless the term 'immediately' or 'directly' is used herein.

When an element or layer is referred to as being "on" other element or layer, it can be immediately on another element or intervening layers or elements may be present. Throughout the specification, the same reference sign indicates the same element.

Although the terms first, second, etc. are used to denote various elements, it is obvious that these elements are not limited by these terms. These terms are only used to distinguish one element from another. Accordingly, it is obvious that a first element mentioned below may be a second element within the technical spirit of the present disclosure.

The size and thickness of each element shown in the drawings are illustrated for convenience of description, and the present disclosure is not necessarily limited to the size and thickness of the elements as shown.

All or some of the features of many embodiments of the present disclosure may be joined or combined together, and as fully understood by those skilled in the art, various interoperations and operations may be technically enabled, and each embodiment may be carried out independently of each other and may be carried out in association with each other.

Hereinafter, a supporting structure (in other words, supporting means or supporting part) with gravity compensation mechanism according to an exemplary embodiment of the present disclosure and an impact control system, and their operation principle will be described with reference to the accompanying drawings. Described below is an impact control system for inducing a traumatic brain injury in an animal for experimentation and a supporting structure with gravity compensation mechanism used in the impact control system, but the present disclosure is not necessarily limited thereto and has a wide range of applications requiring the structure.

Figure 1:
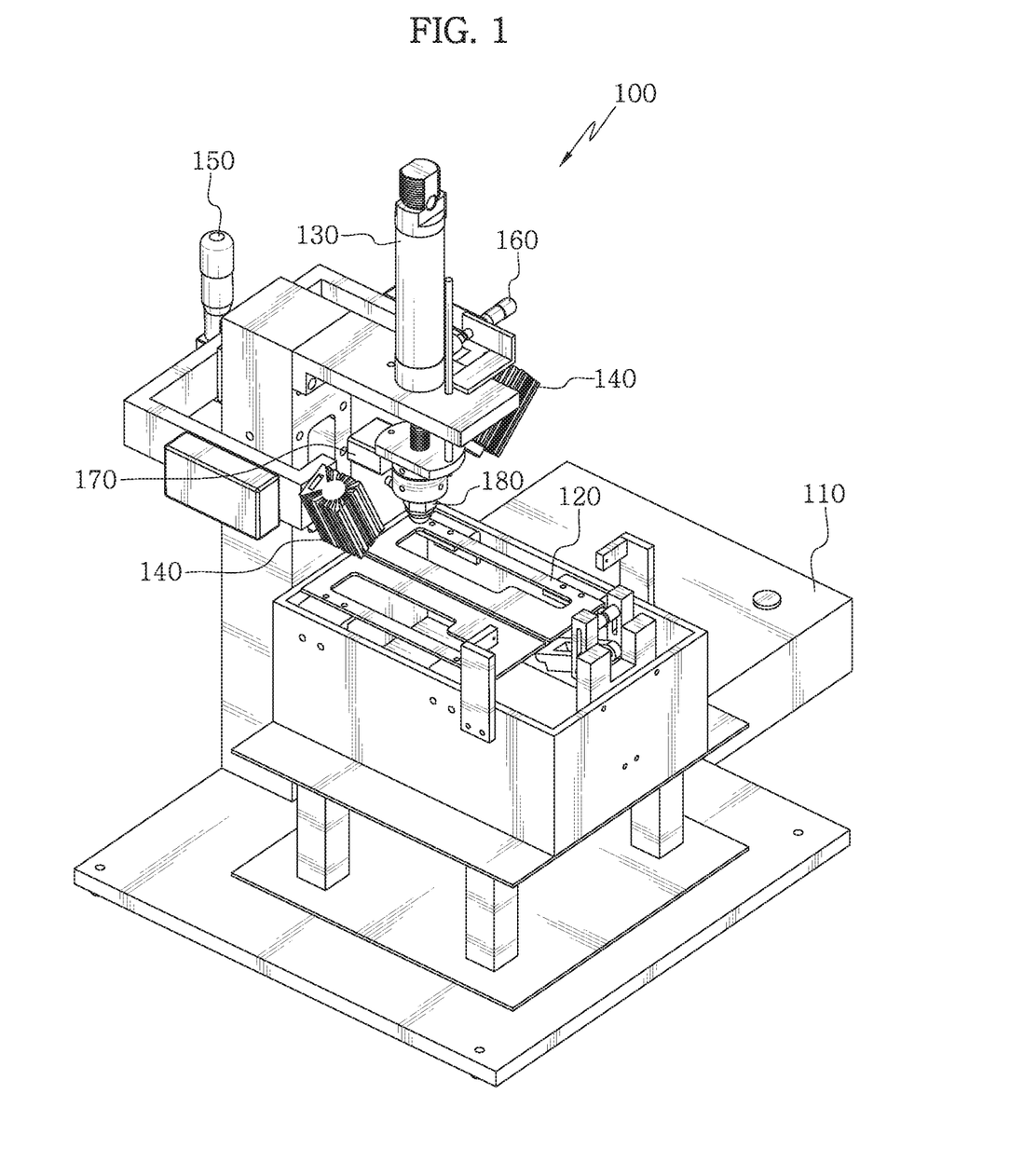
FIG. 1 shows an impact control system according to an embodiment of the present disclosure.

FIG. 1 shows the impact control system 100 according to an embodiment of the present disclosure.

Specifically, referring to FIG. 1, the impact control system 100 according to an embodiment of the present disclosure includes a control device 110, a supporting bed 120, a pneumatic cylinder 130, a target laser 140, a target adjusting device 150, a velocity adjusting device 160, an acceleration sensor 170 and an impact sensor 180.

The control device 110 receives and amplifies a signal measured from the acceleration sensor 170 and the impact sensor 180, and transmits the amplified signal to a computing device (for example, a computer) through a DAQ device. Additionally, the control device 110 may receive a control signal from the computing device through the DAQ device, and control the motion of the piston within the pneumatic cylinder 130. Through the piston motion control, as a result, the movement of an impactor 610 may be controlled. According to another embodiment, the control device 110 includes both the functions of the DAQ device and the computing device to control the impacting and quantitatively calculate an amount of impact by processing profiles measured from the acceleration sensor 170 and the impact sensor 180.

Figure 2:
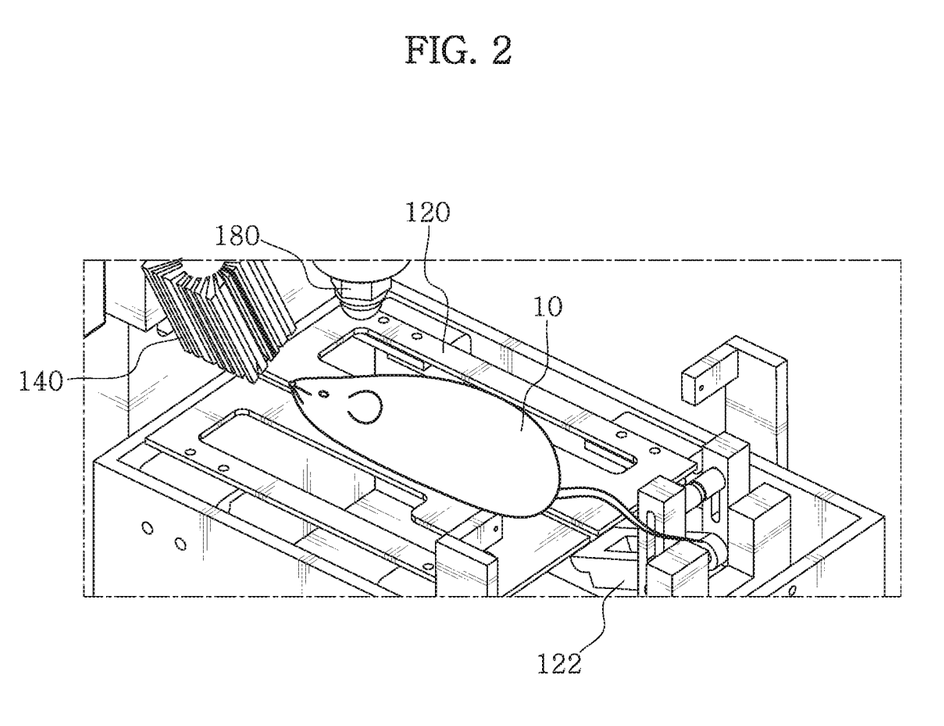
FIG. 2 shows a supporting bed of an impact control system according to an embodiment of the present disclosure.

The supporting bed 120 serves to support a target (e.g., a subject 10) to impact. According to an embodiment of the present disclosure, to prevent the rebound effect (a phenomenon in which a weight strikes the head again by the elastic property of a wire on which the weight hangs) known as the drawback of the weight-drop model, the supporting bed 120 may be configured to split to allow the subject 10 to fall down when impacted. In this instance, as shown in FIG. 2, the supporting bed 120 may withstand the load of the subject 10 by the gravity compensation mechanism through a supporting structure 122 and have a hinge structure on both sides.

The pneumatic cylinder 130 includes the piston that moves by compressed air. According to an embodiment of the present disclosure, the motion of the piston may be controlled by the control device 110.

Figure 6:
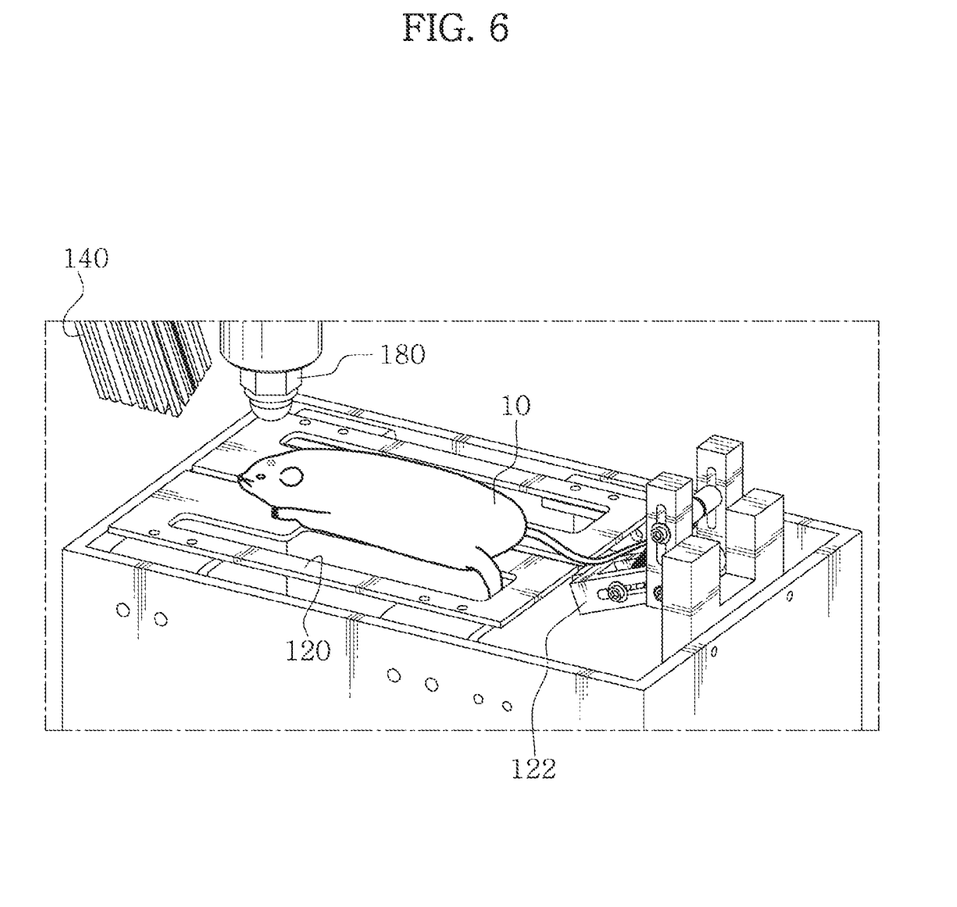
FIG. 6 shows an example of implementation of a supporting bed of an impact control system according to an embodiment of the present disclosure.

The laser beam by the target laser 140 serves to determine a lateral position for impacting, and at the same time, maintain a preset distance between the impactor 610 and the subject 10. According to an embodiment of the present disclosure, an impact position may be set by the target adjusting device 150, and as shown in FIG. 6, two beams of a pair of target lasers 140 tilted left and right are only coincident at the selected distance.

The target adjusting device 150 may adjust the impact position. The target adjusting device 150 may be a micrometer for precisely controlling the impact position. For example, the laser beams of the left and right target lasers 140 may be only coincident at the distance set by the target adjusting device 150, and the impacting may be adjusted by placing the subject 10 at the impact position where the laser beams are coincident.

The velocity adjusting device 160 is a device that adjusts the extent to which a velocity valve is opened by the distance to adjust the impact velocity. For example, the velocity adjusting device 160 may be a micrometer that precisely adjusts the extent to which the velocity valve is opened by the distance. According to an embodiment of the present disclosure, the impact control system 100 may fix the distance between the impactor 610 and the subject 10 by the target adjusting device 150, and use only the velocity adjusting device 160 to control the impact velocity. According to another embodiment, the velocity adjusting device 160 may be omitted, and the computing device such as the computer may set the velocity by digitalization.

The acceleration sensor 170 is a sensor device that measures a change in velocity (acceleration), and may be provided in a base of the impactor 610. According to an embodiment of the present disclosure, an amount of impact may be quantitated by extracting a profile measured by the acceleration sensor 170, comparing it with a profile measured by the impact sensor 180 and extracting an actually applied force. The acceleration sensor 170 may be connected to the control device 110 to transmit the measured signal.

The impact sensor 180 is a sort of force sensor, and may be attached to the end of the impactor that impacts the subject 10. The impact sensor 180 may be a device that is attached to the end of the impactor to measure a force when striking the subject 10. An impactor tip may be further included below the impact sensor 180. The impactor tip may be manufactured in a curved shape, for example, a semispherical shape, to prevent the spread of impact without injuring the subject 10. The impact sensor 180 may be connected to the control device 110 to transmit the measured signal.

According to an embodiment of the present disclosure, it is possible to quantitate an amount of impact by comparing the profiles measured by the acceleration sensor 170 and the impact sensor 180 during impacting and extracting an actually applied force, and precisely apply and measure an impact by controlling the impactor velocity.

FIG. 2 shows the enlarged supporting bed 120 of the impact control system 100 according to an embodiment of the present disclosure. Specifically, referring to FIG. 2, according to an embodiment of the present disclosure, the supporting bed 120 includes the supporting structure 122.

Figure 4:
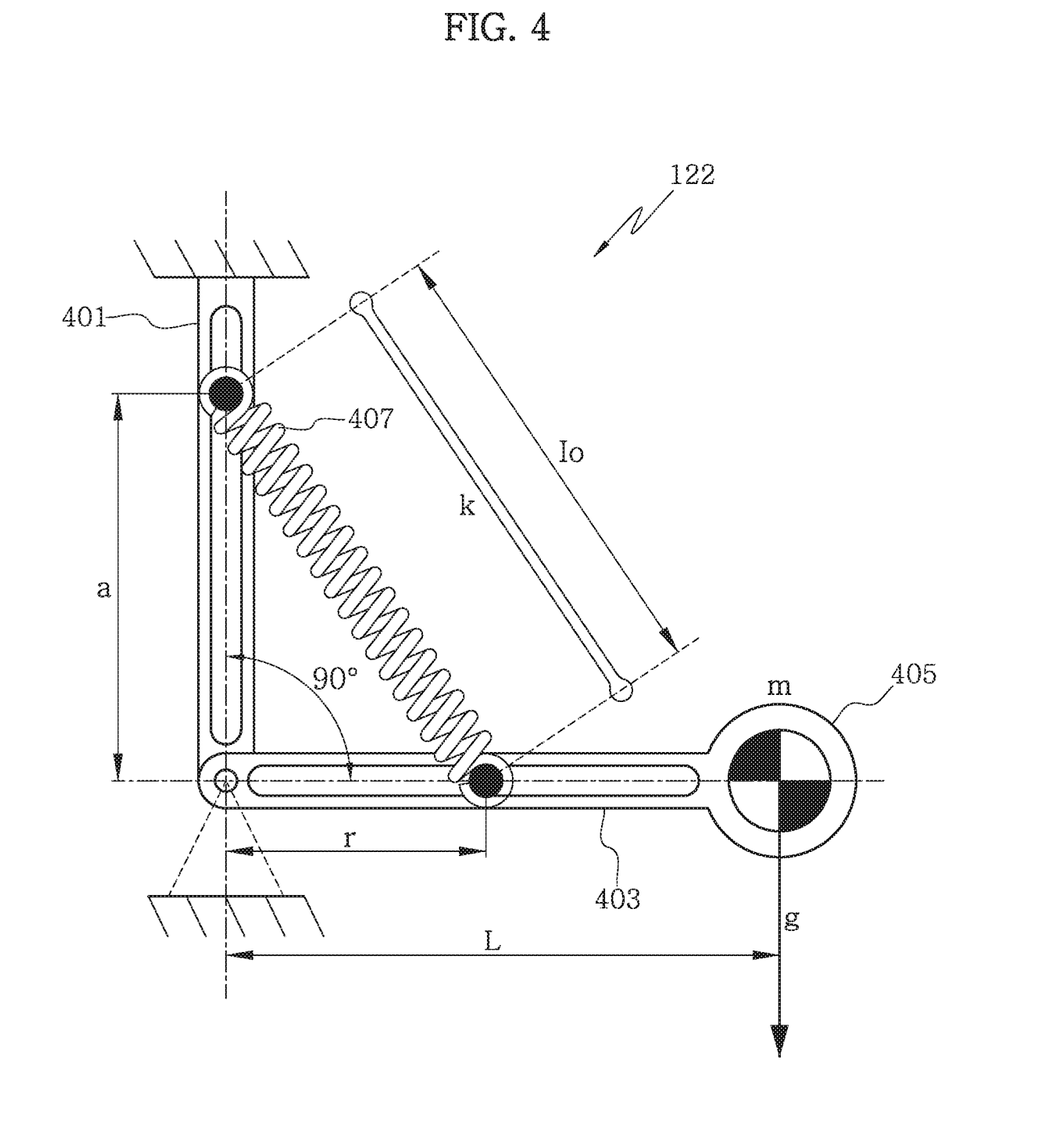
FIG. 4 shows a supporting structure with gravity compensation mechanism according to an embodiment of the present disclosure.
Figure 5:
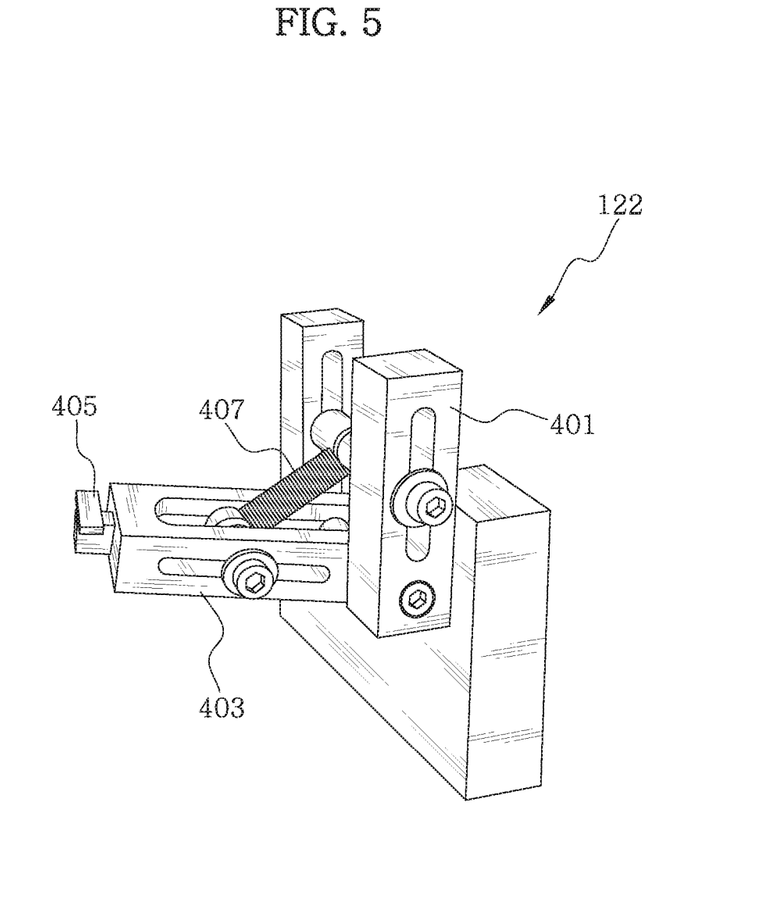
FIG. 5 shows an example of implementation of a supporting structure with gravity compensation mechanism according to an embodiment of the present disclosure.

The supporting structure 122 is configured to compensate for gravity changes by using a spring as shown in FIGS. 4 and 5 so that the torque due to the gravity and the torque due to the elastic force are in equilibrium. This configuration may similarly reproduce the real impacting environment.

In the weight-drop model widely used to study the traumatic brain injury, an anesthetized animal is placed on a foam bed such as a sponge and is impacted on the head by a free fall of a weight disposed on top along a guide tube. However, the greatest drawback of this weight-drop model is the rebound effect that the falling weight strikes the head again.

To overcome this drawback, a method that moves the foam bed itself to a different location quickly after the first impact or a method that places the animal on an aluminum foil has been used.

The method using an aluminum foil is implemented by fixing two side ends of the aluminum foil with a tape, and creating a small scratch in the foil part below the target animal's head using scissors to cause the aluminum foil to be torn off in a fall. This method can remove the rebound effect and mimic a head acceleration model considered important in the traumatic brain injury, and in particular, achieve a rotational acceleration.

However, the problem of this method using an aluminum foil is that impacting may vary depending on the tear volume in the foil (e.g., about 10 mm from the front end) and at which part of the foil the target animal is positioned.

Additionally, to mimic the traumatic brain injury in human occurring in daily life, there is a need for an impact model which is freestanding with no support. Accordingly, to apply a head impact similar to the real one to the anesthetized target animal, the present disclosure proposes the gravity compensation mechanism.

The gravity compensation mechanism refers to a mechanism that instrumentally counterbalances the weight irrespective of a force/torque applied from the outside, and counterbalances the self-weight at any position in relation to a target object using a spring and maintains the position. Gravity compensation devices through springs are cheaper than hydraulic cylinders, and do not increase in driving torque as opposed to the counter-mass. Accordingly, gravity compensation devices through springs are most commonly used in the field of industrial robotics.

Figure 3A:
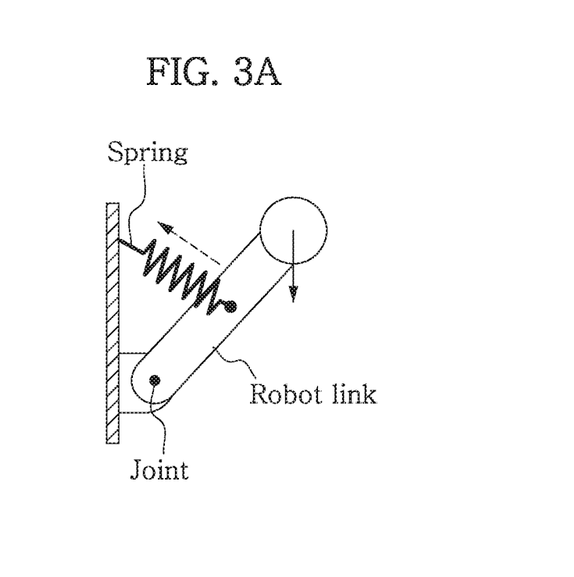
FIGS. 3A to 3C show an embodiment of gravity compensation mechanism in a robotic arm manipulator.
Figure 3B:
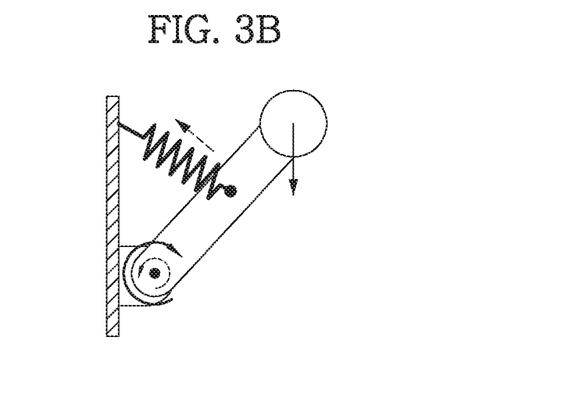
Figure 3C:
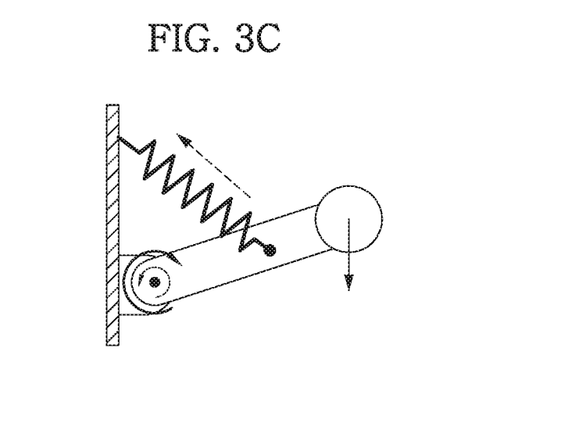

FIGS. 3A to 3C show an embodiment of the gravity compensation mechanism in a robotic arm manipulator. Referring to FIGS. 3A to 3C, the robotic arm manipulator does not need a torque for maintaining the self-weight, and can solve the problem with the controller that is affected by gravity. As shown in FIGS. 3A to 3C, with the rotation of a robot link, the elastic force of the spring changes, and the sum of torques due to the gravity equals the sum of torques due to the spring, so that a target object may counterbalance the self-weight at the changed position and maintain the position.

When the gravity compensation mechanism is applied to the supporting bed for the object, it is possible to support the object of a predetermined range of masses, and maintain the support even though the position of the supporting bed is moved.

The supporting structure with the gravity compensation mechanism has useful applications in systems for applying impacts for the purpose of experiments and treatments. In particular, it is useful for systems requiring precise impacting for animal experiments to study changes in human body caused by external impacts such as traumatic brain injury because of removing the rebound effect on the impacted target subject and reproducing the real impacting environment causing traumatic brain injury.

Hereinafter, the operation principle of the proposed supporting structure with gravity compensation mechanism and an embodiment of the supporting bed of the impact control system having the structure will be described with reference to FIGS. 4 to 6.

FIG. 4 shows the supporting structure 122 with gravity compensation mechanism according to an embodiment of the present disclosure. Referring to FIG. 4, the supporting structure 122 may include a vertical support 401, a horizontal support 403, a weight support part 405 and an elastic element 407.

The vertical support 401 serves to fix one end of the elastic element 407. The distance a from a rotation axis where the end of the vertical support 401 meets one end of the horizontal support 403 to one end of the elastic element 407 may change. To this end, the vertical support 401 may include a sliding hole, and a guide to which one end of the elastic element 407 is fixed may move along the sliding hole of the vertical support 401.

The horizontal support 403 serves to fix the other end of the elastic element 407. The distance r from the rotation axis where the end of the vertical support 401 meets one end of the horizontal support 403 to the other end of the elastic element 407 may change. To this end, the horizontal support 403 may include a sliding hole, and a guide to which the other end of the elastic element 407 is fixed may move along the sliding hole of the horizontal support 403.

The weight support part 405 is configured to support the mass m of the target. That is, the force of gravity m·g due to the mass m of the support target is applied to the weight support part 405 so that the sum of torques due to the gravity and the sum of torques due to the elastic element 407 are in equilibrium, to compensate for gravity. In this instance, the distance L from the rotation axis where the end of the vertical support 401 meets one end of the horizontal support 403 to the weight support part 405 is uniform.

The elastic element 407 is a material having an elastic modulus k, and may have a length lo when the target of the mass m is supported by the weight support part 405. The elastic element 407 may be, for example, a spring. The elastic element 407 does not need to be a spring, and may use any elastic material having a predetermined restoring force when its length increases or decreases. For example, the elastic modulus k of the elastic element 407 (e.g., the spring) is determined, taking into account the distance r from the rotation axis to the other end of the elastic element 407, the distance L from the rotation axis to the weight support part 405 and the range of mass m of the target to support.

According to an embodiment of the present disclosure, when the supporting structure 122 includes the elastic element 407 having a predefined elastic modulus k, the distance r from the rotation axis to the other end of the elastic element 407 may be changed to change the range of mass m supported.

FIG. 5 shows an example of implementation of the supporting structure 122 with gravity compensation mechanism according to an embodiment of the present disclosure.

Referring to FIG. 5, the supporting structure 122 is designed such that one end of the elastic element 407 is fixed to the vertical support 401 and the other end of the elastic element 407 is fixed to the horizontal support 403, so that the sum of torques due to the elastic element 407 and the sum of torques due to the gravity are in equilibrium, to allow the weight support part 405 to maintain the balance at the moved position. An element to which one end of the elastic element 407 is fixed and an element to which the other end of the elastic element 407 is fixed may move along the sliding hole of the vertical support 401 and the sliding hole of the horizontal support 403 respectively according to the mass of the support target and may be fixed in position. Through this, it is possible to change the supportable mass of the target by the supporting structure 122 without replacing with an elastic element 407 having a different elastic modulus k.

The weight support part 405 may directly support the target, and may support the target through gravity compensation by indirectly supporting a plate that supports the target. For example, the weight support part 405 is preferably configured to support the target by putting the target support plate thereon, and as shown in FIG. 5, may include a concave groove for putting the target support plate.

FIG. 6 shows an example of implementation of the supporting bed 120 of the impact control system 100 according to an embodiment of the present disclosure.

Referring to FIG. 6, the supporting structure 122 supports the supporting bed 120, and the supporting bed 120 supports the subject 10, thereby enabling support for precise impacting.

The supporting structure 122 includes the vertical support 401, the horizontal support 403, the weight support part 405 and the elastic element 407 to which the above-described gravity compensation mechanism is applied. The supporting bed 120 is supported by the underlying weight support part 405 of the supporting structure 122 to withstand the load of the subject 10. According to an embodiment of the present disclosure, the supporting bed 120 includes a plurality of support plates, and one end of each plate may be designed in a hinge structure. For example, as shown in FIG. 6, the supporting bed 120 includes two support plates designed with two ends of each support plate formed in a hinge structure, opening downward, like sliding doors. In this case, when an impact is applied to the subject 10, the supporting structure 122 withstanding the load of the subject 10 is out of balance, the supporting bed 120 is split in a direction (e.g., a down direction) in which the impact is applied, and the subject 10 falls down. In the real animal experiment, the subject 10 may be supported without any adjustment due to the tolerance of the mechanism within a predetermined range (e.g., 18-28 g), but when there is a great change in the load of the subject 10, it is possible to adjust by moving the initial position of the elastic element 407 along the sliding holes of the vertical support 401 and the horizontal support 403 to compensate for a mass difference. According to an embodiment of the present disclosure, each of the support plates of the supporting bed 120 may be manufactured with a hole by removing the central area. When the support plates are manufactured in such a shape, the support plates reduce in weight, facilitating the design and making it easier to place the target.

As described above, it is possible to reproduce an environment in which a similar impact to the real one is applied without the rebound effect through the supporting structure with gravity compensation mechanism.

In the above-described specific embodiments, the elements are expressed as singular or plural forms according to the specific embodiments presented herein. However, the singular or plural forms are suitably selected for the presented situations for convenience of description, the above-described embodiments are not limited to single or many elements, and elements expressed as plural forms may be singular and elements expressed as singular forms may be plural.

Although specific embodiments have been described in the detailed description, it is obvious that many modifications may be made without departing from the technical spirit and scope of various embodiments. Therefore, the scope of the present disclosure should not be limited to the disclosed embodiments and should be defined by the appended claims and equivalents thereto.

[Detailed Description of Main Elements]

| | |
|---|---|
| 10: Subject | 100: Impact control system |
| 110: Control device | 120: Supporting bed |
| 122: Supporting structure | 130: Pneumatic cylinder |
| 140: Target laser | 150: Target adjusting device |
| 160: Velocity adjusting device | 170: Acceleration sensor |
| 180: Impact sensor | 401: Vertical support |
| 403: Horizontal support | 405: Weight support part |
| 407: Elastic element | |

What is claimed is:

1. An impact control system, comprising:
a supporting structure with gravity compensation mechanism; and
a supporting bed which is supported by the supporting structure and supports an impact target,
wherein the supporting structure comprises:
    an elastic element;
    a vertical support to which one end of the elastic element is coupled;
    a horizontal support to which the other end of the elastic element is coupled, and which is rotatable around a rotation axis disposed at one end of the horizontal support meeting an end of the vertical support; and
    a weight support part which is connected to the other end of the horizontal support and supports the supporting bed while contacting a lower surface of the supporting bed.

2. The impact control system according to claim 1, wherein each of the vertical support and the horizontal support includes a sliding hole.

3. The impact control system according to claim 2, wherein a guide to which one end of the elastic element is coupled is configured to be moveable along the sliding hole of the vertical support,
    a guide to which the other end of the elastic element is coupled is configured to be moveable along the sliding hole of the horizontal support, and
    a supportable mass of the target is changed by moving the guides of the elastic element.

4. The impact control system according to claim 1, wherein the elastic element is a spring.

5. The impact control system according to claim 1, wherein the supporting bed includes two support plates, and each of the support plates has one end of a hinge structure.

6. The impact control system according to claim 5, wherein when an impact is applied to the target, the weight support part of the supporting structure moves down to allow the two support plates of the supporting bed to split down and the target to fall down.

7. The impact control system according to claim 5, wherein each of the support plates includes a hole formed by removing a central area of the plate.

\* \* \* \* \*